US00PP11809P2

(12) United States Plant Patent
Wojciechowski

(10) Patent No.: US PP11,809 P2
(45) Date of Patent: Mar. 13, 2001

(54) VINCA PLANT NAMED 'WOJO'S JEM'

(75) Inventor: Joseph Henry Wojciechowski, Ortonville, MI (US)

(73) Assignee: Wojo's Greenhouse, Ortonville, MI (US)

( * ) Notice: Subject to any disclaimer, the term of this patent is extended or adjusted under 35 U.S.C. 154(b) by 0 days.

(21) Appl. No.: 09/396,484

(22) Filed: Sep. 15, 1999

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Vinca plant named 'Wojo's Jem', characterized by its unique ivory and dark green-colored variegated foliage with ivory at leaf center surrounded by dark green margin; and decumbent, trailing and freely branching growth habit.

2 Drawing Sheets

BACKGROUND OF THE INVENTION

The present invention relates to a new and distinct cultivar of Vinca plant, botanically known as *Vinca maculata*, and hereinafter referred to by the cultivar name 'Wojo's Jem'.

The new Vinca is a naturally-occurring branch sport of an unidentified selection of *Vinca maculata* (not patented) with solid green leaves. The new Vinca was discovered and selected by the Inventor in March, 1996, within a population of plants of the unidentified *Vinca maculata* selection grown in a cultivated area in Ortonville, Mich. The new Vinca was selected on the basis of its unique variegated foliage.

Asexual reproduction of the new cultivar by terminal cuttings taken at Ortonville, Mich., has shown that the unique features of this new Vinca are stable and reproduced true to type in successive generations.

SUMMARY OF THE INVENTION

Plants of the cultivar 'Wojo's Jem' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Wojo's Jem'. These characteristics in combination distinguish 'Wojo's Jem' as a new and distinct cultivar.

1. Unique ivory and dark green-colored variegated foliage; ivory at leaf center surrounded by dark green margin.
2. Decumbent, trailing and freely branching growth habit.

Plants of the new Vinca differ from plants of unidentified selections of the variegated *Vinca major* as plants of the new Vinca have leaves with ivory-colored centers currounded by dark green-colored margins whereas plants of the unidentified selection of the variegated *Vinca major* have leaves with green-colored centers surrounded by ivory-colored margins.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical container of the new Vinca.

The photograph on the second sheet comprises a side perspective view of typical plants of an unidentified selection of *Vinca major*, the new Vinca, and an unidentified selection of *Vinca maculata* (left to right). Foliage colors in the photographs may appear different than the actual colors due to light reflectance.

DETAILED BOTANICAL DESCRIPTION

In the following description, color references are made to The Royal Horticultural Society Colour Chart except where general terms of ordinary dictionary significance are used.

Plants used for the description were grown for about 8 weeks in 12.5-cm containers in greenhouses covered with a double layer of polyethylene with day and night temperatures of about 20 and 18° C., respectively, during the late spring/early summer in Ortonville, Mich.

Botanical classification: *Vinca maculata* cultivar 'Wojo's Jem'.

Parentage: Naturally-occurring branch sport of an unidentified selection of *Vinca maculata* (not patented).

Propagation:

- *Type cutting.*—Vegetative cuttings.
- *Time to initiate roots, summer.*—About 18 days at 24° C.
- *Time to initiate roots, winter.*—About 21 days at 22° C.
- *Time to produce a rooted cutting, summer.*—About 35 days at 24° C.
- *Time to produce a rooted cutting, winter.*—About 42 days at 22° C.
- *Root description.*—Numerous, fine, fibrous, and well-branched.

Plant description:

- *Form.*—Decumbent, trailing and cascading; suitable for hanging basket containers.
- *Branching habit.*—Freely basally branching. Pinching enhances lateral branch development.
- *Vigor.*—Moderately vigorous.

*Plant height* (*from soil level to top top of plant plane*). —About 15 cm.

*Spreading area of plant.*—About 30 cm.

*Stem description.*—Length: About 30 cm; indeterminate. After four or five months of growth, stems may attain a length of about one meter. Diameter: About 2.5 mm. Internode length: About 3.5 cm. Strength: Wiry and flexible when young; mature, moderately strong and flexible. Color: Ivory, 4D with some anthocyanin, close to 46A.

*Foliage description.*—Leaves simple, opposite, generally symmetrical and long persisting. Length: About 5.5 cm. Width: About 5.1 cm. Aspect: Perpendicular to stem. Shape: Broadly ovate. Apex: Rounded to dentate. Base: Truncate. Margin: Entire. Texture: Smooth, glabrous. Color: Typically ivory-colored centers with green margins; actual variegation pattern is irregular. Young foliage upper surface: Center, ivory, 4C to 4D; margin, dark green, 147A or darker. Young foliage lower surface: Center, ivory, 4C to 4D; margin, greener than 146A; occasionally interspersed with green, 146C, spots. Mature foliage upper surface: Center, ivory, 4C to 4D; margin, dark green, 147A or darker; occasionally interspersed with green, 146A, spots. Mature foliage lower surface: Center, ivory, 4D; margin, greener than 146A; occasionally interspersed with dulled green, close to 194A, spots. Petiole: Length: About 1.3 cm. Diameter: About 2 mm. Aspect: Convex. Color: 4C to 4D.

Flower description: Flower development has not been observed to date.

Disease resistance: Resistance to diseases common to Vinca has been observed.

Seed production: Seed production has not been observed.

It is claimed:

1. A new and distinct cultivar of Vinca plant named 'Wojo's Jem', as illustrated and described.

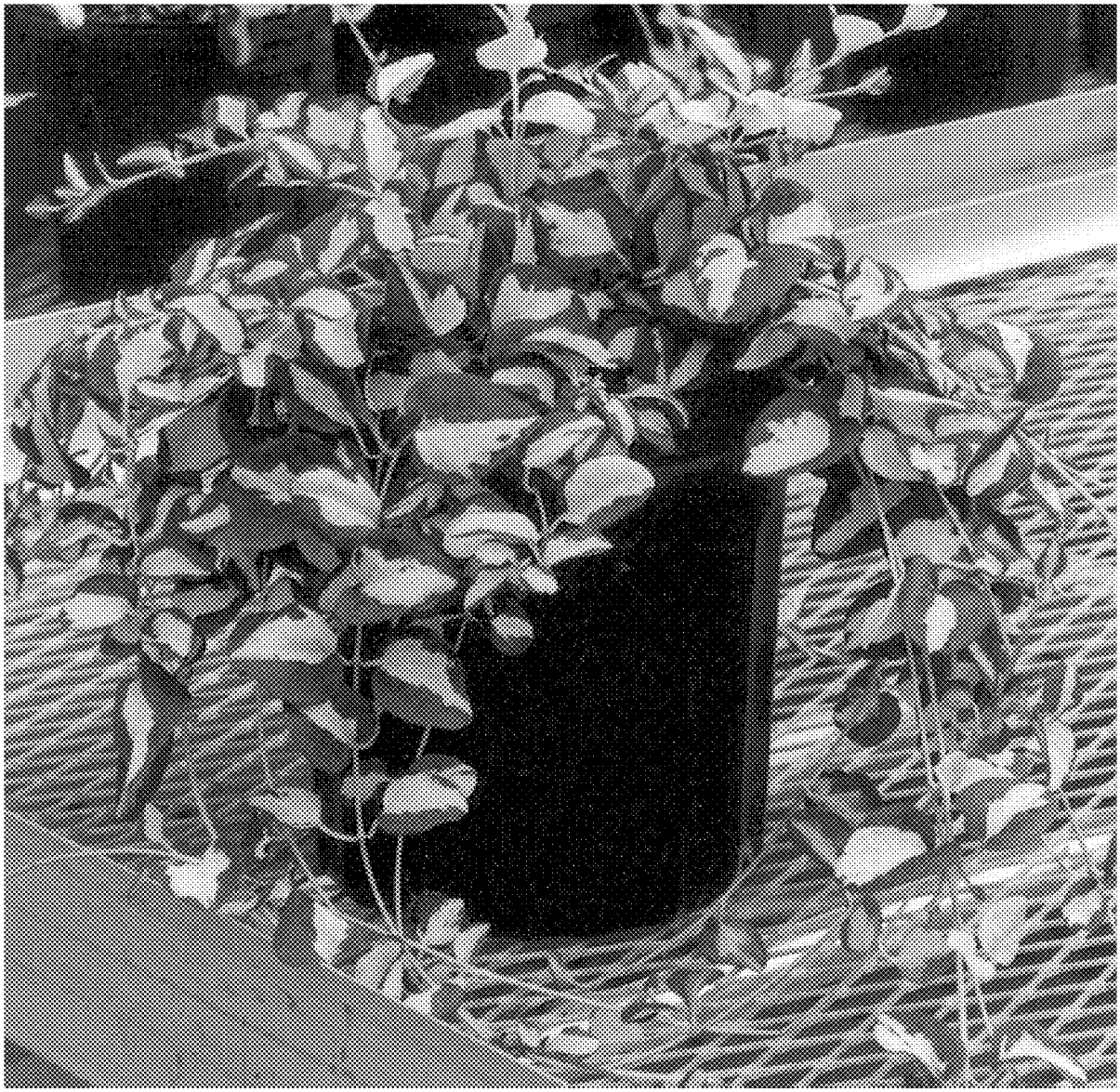

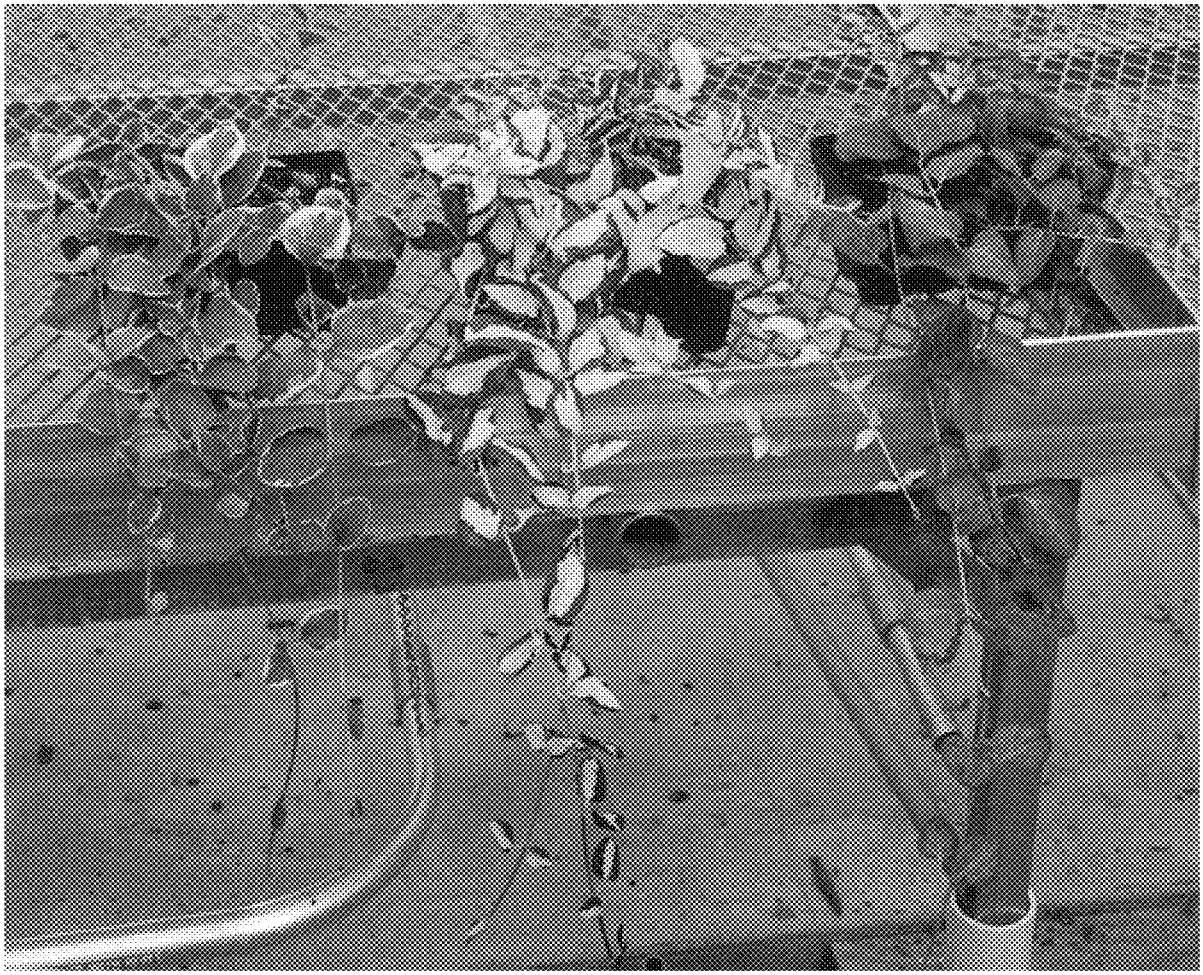

* * * * *